United States Patent
Cox

[11] Patent Number: 6,085,989
[45] Date of Patent: Jul. 11, 2000

[54] SCENT DISPENSER AND METHOD

[76] Inventor: Larry R. Cox, 5540 Sullivantown Rd., Walkertown, N.C. 27051

[21] Appl. No.: 09/190,972

[22] Filed: Nov. 9, 1998

[51] Int. Cl.[7] .................................................. A24F 25/00
[52] U.S. Cl. ............................................................. 239/59
[58] Field of Search ................................. 239/55, 56, 58, 239/89

[56] References Cited

U.S. PATENT DOCUMENTS

| | | | |
|---|---|---|---|
| 2,556,608 | 6/1951 | T. Will | 239/58 |
| 2,738,225 | 3/1956 | G. W. Meek | 239/59 |
| 3,046,192 | 7/1962 | Bilyeu | 167/48 |
| 4,472,377 | 9/1984 | Teranishi et al. | 424/84 |
| 4,506,806 | 3/1985 | Lincoln et al. | 222/175 |
| 4,523,717 | 6/1985 | Schwab | 239/56 |
| 4,523,870 | 6/1985 | Spector | 239/59 |
| 4,609,245 | 9/1986 | Sakschek | 239/36 |
| 4,667,430 | 5/1987 | Ziese, Jr. | 43/1 |
| 4,771,563 | 9/1988 | Easley | 43/1 |
| 4,773,177 | 9/1988 | Gray, II et al. | 43/1 |
| 4,788,787 | 12/1988 | Konietzki | 43/1 |
| 4,944,940 | 7/1990 | Christenson, II | 424/84 |
| 4,953,763 | 9/1990 | Kierum et al. | 222/644 |
| 4,989,547 | 2/1991 | Eaton | 119/51.11 |
| 5,094,025 | 3/1992 | Daniels | 43/1 |
| 5,148,949 | 9/1992 | Luca | 222/175 |
| 5,305,541 | 4/1994 | Simpson | 43/1 |
| 5,369,903 | 12/1994 | Cox | 43/1 |
| 5,678,763 | 10/1997 | Scheuer et al. | 239/59 |

*Primary Examiner*—Andres Kashnikow
*Assistant Examiner*—Christopher S. Kim

[57] ABSTRACT

Disclosed herein is a scent dispenser comprised of a pair of transparent, telescopingly polymeric sleeves, each of the sleeves defining eight apertures. The apertures are selectively aligned for scent emission in various configurations. Contained within the scent dispenser is a scent producing substance which emits scent which travels through the apertures when appropriately aligned. A system of nubs and projections engage to allow the selective positioning of the sleeves relative to one another.

14 Claims, 3 Drawing Sheets

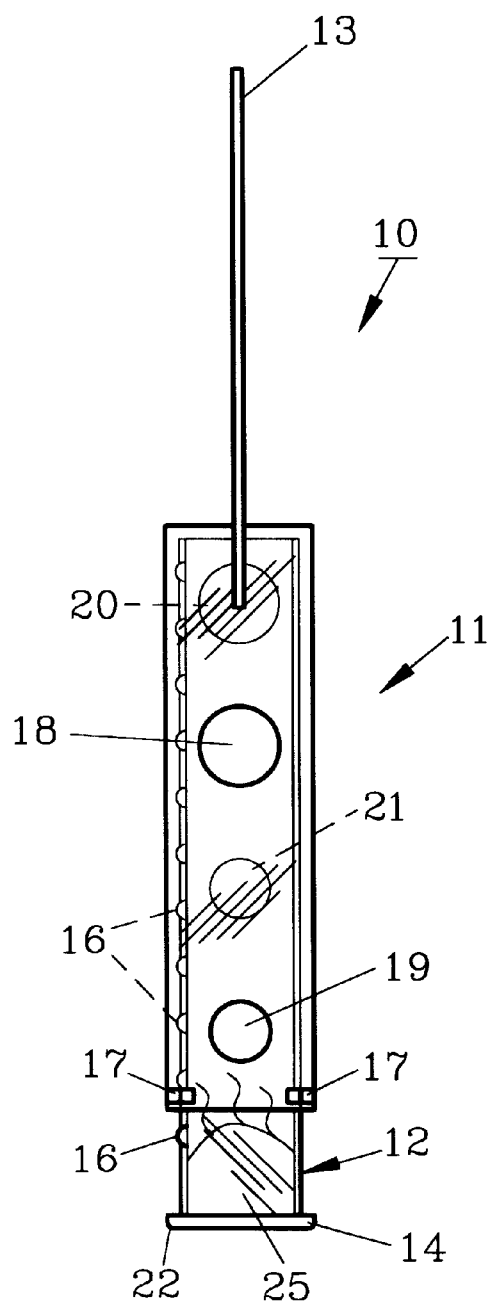
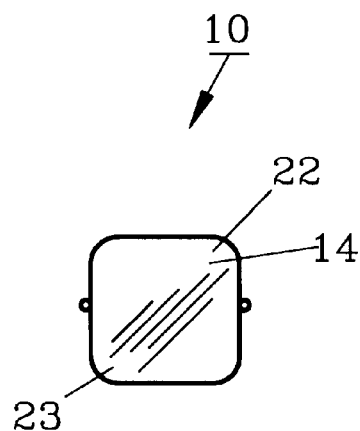
FIG. 4
FIG. 3

SCENT DISPENSER AND METHOD

BACKGROUND OF THE INVENTION

1. Field of the Invention

This invention pertains to a tubular scent dispenser for hunting as may be used in hunting deer or other game.

2. Description of the Prior Art and Objectives of the Invention

Hunters are every ready to try something new with which to attract prey during hunting season. Scent dispensers such as that disclosed in my copending application Ser. No. 08/980,291, filed Nov. 28 1997, are used with some success. These dispensers bring prey close to the hunter's stand where it may be easily viewed, photographed or shot.

However, many such devices are expensive or otherwise undesirable. Thus, it is an objective of the present invention to provide an inexpensive scent dispenser and method of use.

It is a further objective of the present invention to provide a device which is essentially fool proof to operate and position.

It is still a further objective of the present invention to provide a device which can adjustably emit a desired scent and which can be closed to prevent emission as desired.

These and other objectives and advantages will become readily apparent to those skilled in the art upon reference to the following detailed description and accompanying drawing figures.

SUMMARY OF THE INVENTION

The aforedescribed objectives and advantages are realized by providing a rectilinear, telescoping tubular scent dispenser. The scent dispenser comprises a first and a second sleeve, wherein the first sleeve slidingly engages nubs on the second sleeve for selective positioning thereon. Each sleeve defines preferable eight apertures, two on each side of the two rectilinear sleeves When the apertures are coincidentally aligned, a scent drifts from the interior of the scent dispenser to the exterior and surrounding environment thereby potentially attracting prey to the location of the scent dispenser.

BRIEF DESCRIPTION OF THE DRAWINGS

FIG. 3 demonstrates a side elevational view of the closed scent dispenser of FIG. 1;

FIG. 4 features a bottom view of the scent dispenser of FIG. 1; and

DETAILED DESCRIPTION OF THE PREFERRED EMBODIMENT AND OPERATION OF THE INVENTION

Figure 1:
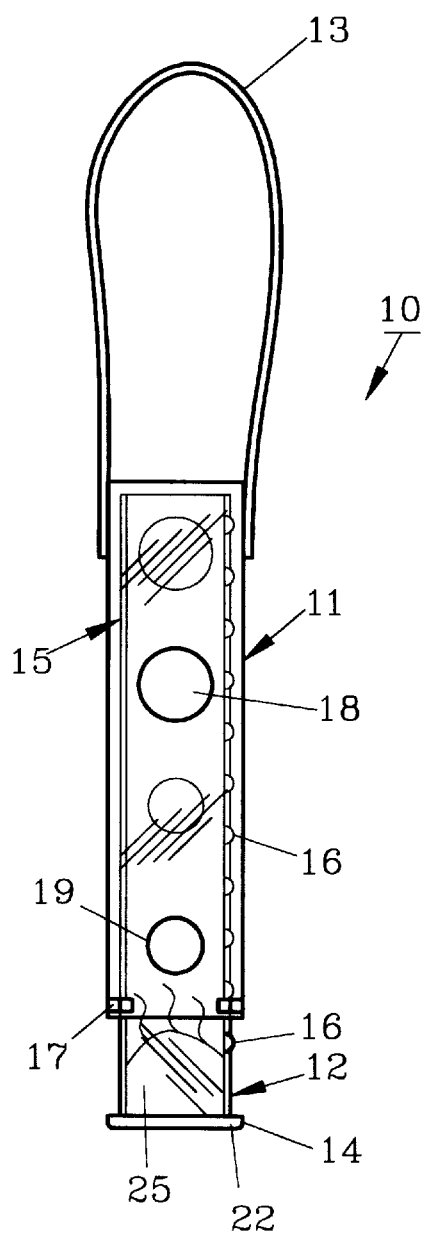
FIG. 1 shows a front elevational view of the scent dispenser in a closed position.
Figure 2:
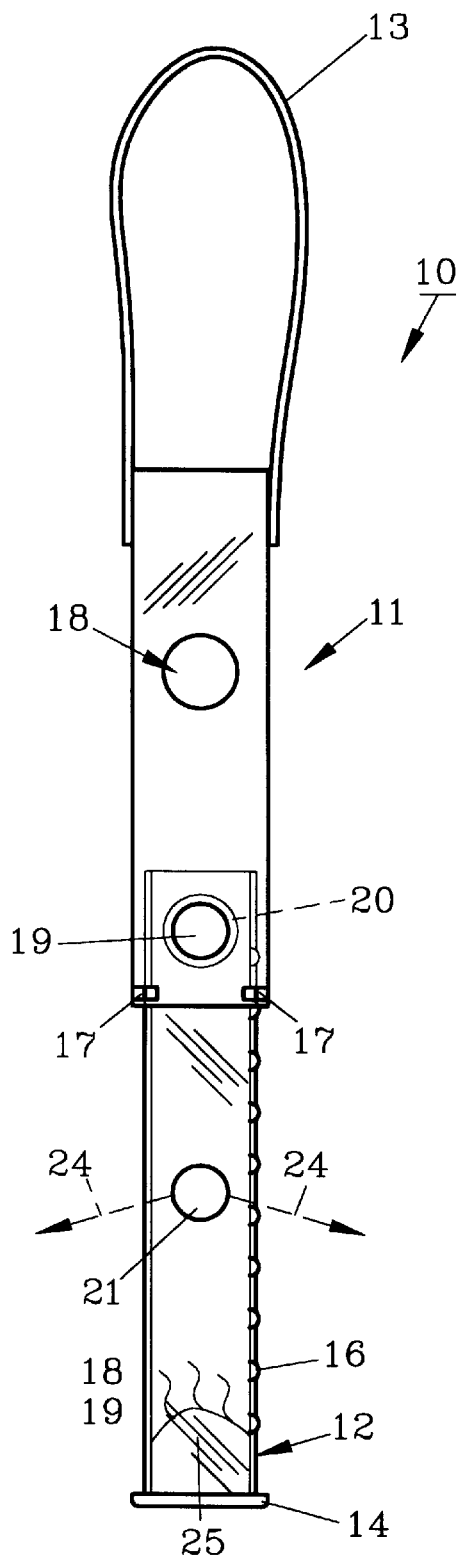
FIG. 2 illustrates the scent dispenser of FIG. 1, but in one open, active position.

Turning now to the drawings, specifically FIGS. 1–4 shows preferred scent dispenser 10, which is generally a box-like container and comprises rectilinear first outer sleeve 11, second inner rectilinear sleeve 12, flexible loop 13 and base 14. Flexible loop 13 is attached to first sleeve 11 proximate top 15. First sleeve 11 defines large aperture 18 and small aperture 19 on each of its four faces. Likewise, second sleeve 12 defines small aperture 21 and large aperture 20 on each of its four faces (FIG. 3). Apertures 19 and 21 are generally smaller than apertures 18 and 20 for precise scent emission adjustment purposes. Second sleeve 12 also includes nubs 16 on two opposite corners 22, 23 (FIG. 4) of its rectilinear structure. Nubs 16 engage projections 17 inside first sleeve 11. Thus, the method of use allow second sleeve 12 to be telescopingly, selectively positioned along first sleeve 11. Each sleeve is preferably approximately 2.75 inches (7 cm) long and ½ inch (1.27 cm) square.

Figure 5:
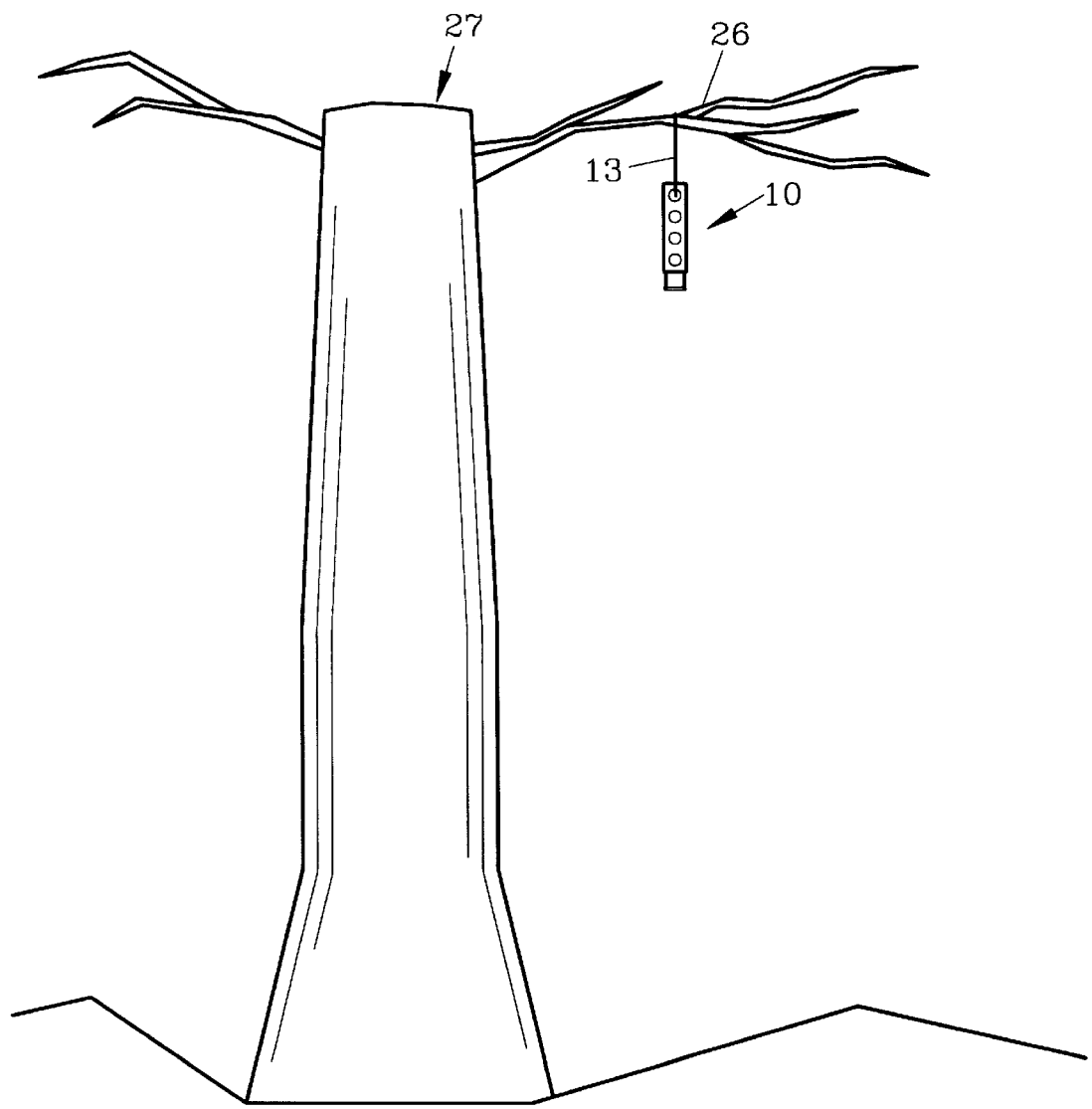
FIG. 5 depicts the scent dispenser in use on a tree.

Nubs 16 and projections 17 engage with projection 17 between pairs of nubs 16 as is conventional to allow apertures 18–21 to be aligned selectively and permit scent 24 emitted from scent producing means 25 to escape from scent dispenser 10 and attract prey. For example, in the method of use apertures 18 may align with apertures 20 and apertures 19 simultaneously align with apertures 21. Thus three, two or one opening on each side is possible, as are partial openings for scent emission, depending on the particular scent employed and the amount of scent release required. In each case, scent 24 drifts from the opened scent dispenser 10 and potentially attracts game for the hunter. Scent dispenser 10 is preferably a clear polymeric material such a polyethylene. As seen in FIG. 5 scent dispenser 10 is hung from branch 26 of tree 27 by flexible loop 13. Scent producing means 25 may be a cotton ball saturated with a liquid scent as commercially available.

The preceding recitation is provided as an example of the preferred embodiment and is not intended to limit the nature of scope of the present invention or appended claims.

I claim:

1. A scent dispenser comprising an inner sleeve and an outer sleeve, said outer sleeve telescopingly positioned over said inner sleeve, said inner sleeve and said outer sleeve each defining a plurality of different size apertures for scent emission therethrough.

2. The scent dispenser of claim 1 wherein said inner sleeve is rectangularly shaped and comprises a plurality of nubs.

3. The scent dispenser of claim 2 wherein said outer sleeve is rectangularly shaped and comprises projections for engaging said nubs for precise alignment of said inner and outer sleeves.

4. The scent dispenser of claim 1 further comprising a flexible loop, said flexible loop attached to said outer sleeve.

5. The scent dispenser of claim 1 wherein said inner sleeve is formed from a polymeric material and defines a pair of different size apertures.

6. The scent dispenser of claim 1 wherein said outer sleeve is formed from a polymeric material and defines a pair of different size apertures.

7. The scent dispenser of claim 6 wherein said inner sleeve apertures can be positioned in selective coincidental alignment with said apertures of said outer sleeve.

8. The scent dispenser of claim 1 further comprising scent producing means, said scent producing means contained within said inner sleeve.

9. The scent dispenser of claim 1 wherein said outer sleeve defines a large upper aperture and a small lower aperture and said inner sleeve defines a large lower aperture and a small upper aperture.

10. A method of scent emission from a dispenser for attracting game during hunting comprising the steps of:
   (a) placing scent producing matter in an inner apertured sleeve having a plurality of different size apertures therein;
   (b) sliding an outer apertured sleeve having a plurality of different size apertures therein over said inner sleeve; and (c) allowing a scent to emit from said inner sleeve by coincidentally aligning apertures of said inner and said outer sleeves.

11. The method of claim 10, further comprising the step of adjusting the outer sleeve to totally expose an aperture.

12. The method of claim 11, wherein adjusting the outer sleeve comprises the step of coincidentally aligning a small aperture on said inner sleeve with a large aperture on said outer sleeve.

13. The method of claim 10 further comprising the step of suspending said scent dispenser above the ground with a flexible loop.

14. The method of claim 13 wherein suspending said scent dispenser comprises the step of suspending said scent dispenser from a tree.

* * * * *